United States Patent
Wölfert et al.

(10) Patent No.: US 6,833,469 B2
(45) Date of Patent: Dec. 21, 2004

(54) METHOD FOR PRODUCING ISOCYNATES

(75) Inventors: Andreas Wölfert, Bad Rappenau (DE); Christian Müller, Mannheim (DE); Eckhard Stroefer, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/480,240

(22) PCT Filed: Jun. 6, 2002

(86) PCT No.: PCT/EP02/06196

§ 371 (c)(1),
(2), (4) Date: Dec. 10, 2003

(87) PCT Pub. No.: WO02/102763

PCT Pub. Date: Dec. 27, 2002

(65) Prior Publication Data

US 2004/0192959 A1 Sep. 30, 2004

(30) Foreign Application Priority Data

Jun. 19, 2001 (DE) ......................................... 101 29 233

(51) Int. Cl.[7] .............................................. C07C 263/00
(52) U.S. Cl. ...................................... 560/347; 560/338
(58) Field of Search ................................. 560/338, 347

(56) References Cited

U.S. PATENT DOCUMENTS 2,822,373 A   2/1958   Beck
5,925,783 A   7/1999   Jost et al.

FOREIGN PATENT DOCUMENTS

| | | |
|---|---|---|
| DE | 1 192641 | 5/1965 |
| DE | 2 252068 | 5/1973 |
| GB | 1341311 | 12/1973 |
| WO | 96/16028 | 5/1996 |

*Primary Examiner*—Paul J. Killos
(74) *Attorney, Agent, or Firm*—Keil & Weinkauf

(57) ABSTRACT

The invention relates to a process for the production of isocyanates by reaction of primary amines with phosgene, in which isocyanate is used as solvent, wherein some or all of isocyanate used as solvent is added to the reaction mixture only after the amine and phosgene have been physically combined.

7 Claims, 2 Drawing Sheets

METHOD FOR PRODUCING ISOCYNATES

DESCRIPTION

Figure 1:
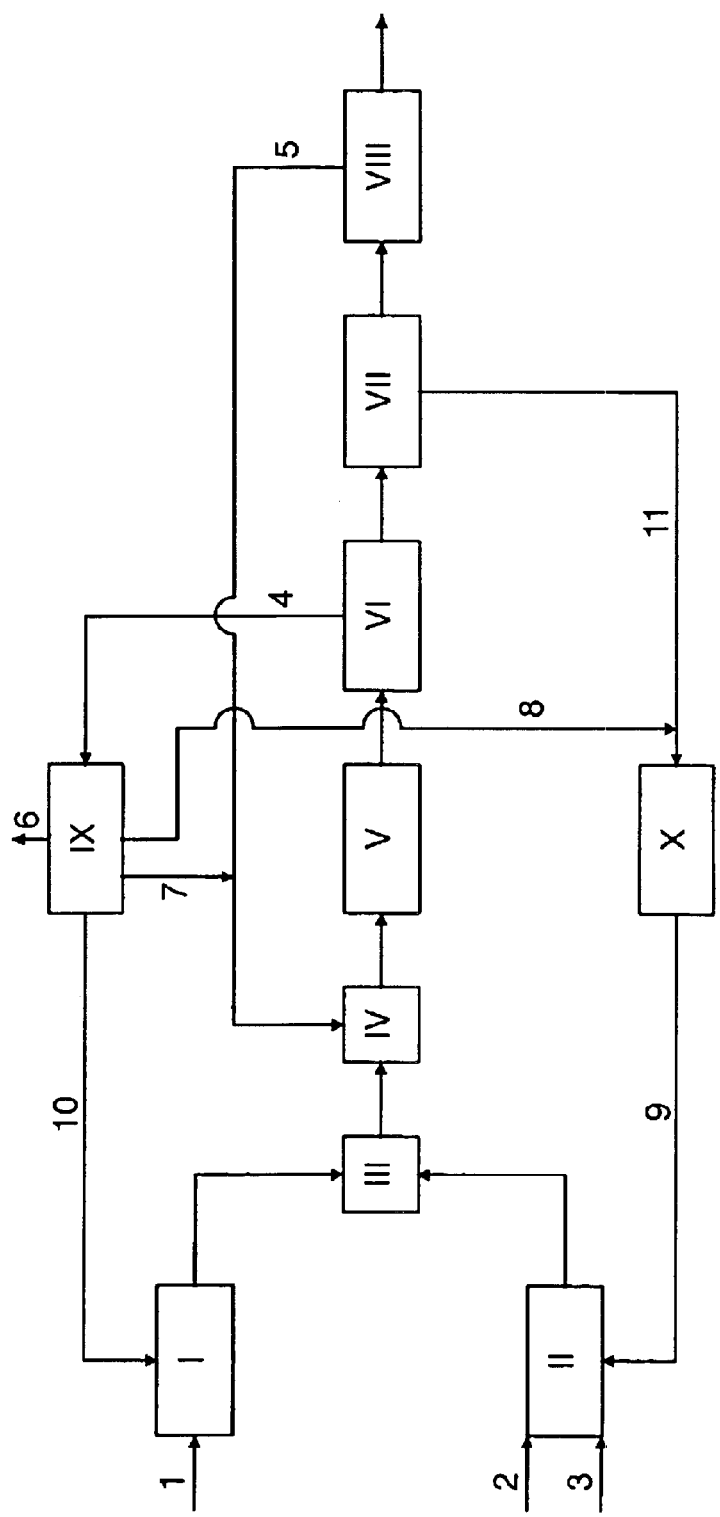

The present invention relates to a process for the production of isocyanates by reaction of amines with phosgene using isocyanate as solvent, the isocyanate used as solvent being added to the reaction mixture only after the amine and phosgene have been physically combined.

Various processes for the production of isocyanates by reaction of amines with phosgene in the presence of isocyanate are known.

DE-A 1,192,641 describes a process for the production of isocyanates by reaction of amines with phosgene, the isocyanate produced during the reaction being used as solvent for phosgene.

DE-A 2,252,068 describes a process for the production of organic isocyanates, wherein amine is caused to react with preheated phosgene in the presence of an excess of isocyanate at temperatures and pressures selected so as to give a homogeneous liquid phase.

U.S. Pat. No. 2,822,373 describes a continuous process for the production of isocyanates, in which a phosgene solution is mixed with a solution of an organic amine in a turbulent reactor circulation system. In this case, the fresh phosgene solution is combined with the circulated reaction solution prior to blending with the amine solution.

WO 96/16028 describes a continuous process for the production of isocyanates by reaction of corresponding primary amines with phosgene in the presence of an isocyanate acting as solvent, wherein the amine is caused to react with phosgene, which is dissolved in the isocyanate in a concentration of from 10 to 60 wt %.

It is also known that the use of a high phosgene excess over the amino groups used leads to high selectivities toward the isocyanate produced and can thus have a decisive influence on the economical value of the process. However, with an increasing ratio of phosgene to amino groups there is a rise in the phosgene holdup of the plant, which should, however, be minimized on account of the toxicity of phosgene.

It is thus an object of the present invention to provide a process for the production of isocyanates which makes it possible to carry out the reaction with high selectivity without raising the phosgene hold-up or lowering the space-time yield.

The object of the invention is achieved, unexpectedly, in the production of isocyanates by the reaction of amine with phosgene, by adding an isocyanate as solvent, which solvent is added not, as described in the prior art, to the phosgene prior to the reaction, but to the reaction mixture formed by physically combining the phosgene and amine.

Thus the present invention relates to a process for the production of isocyanates by reaction of primary amines with phosgene, in which isocyanate is used as solvent, wherein some or all of the isocyanate used as solvent is added to the reactants only when the amine and phosgene have been physically combined.

The process of the invention includes continuous, semicontinuous, and batch processes. Preference is given to continuous processes. During the production of isocyanate by reaction of a primary amine with phosgene there is formed, in an initial fast step, α-cording to following reaction scheme, the intermediate carbamoyl chloride, which decomposes in the rate-determining, slow step in a balanced reaction to form isocyanate and HCl.

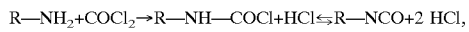

R—NH$_2$+COCl$_2$→R—NH—COCl+HCl⇌R—NCO+2 HCl, in which R is an organic radical.

Furthermore the resulting hydrogen chloride can react with amines to form amine hydrochlorides.

The essential feature of the process of the invention is that the addition of the isocyanate acting as solvent does not occur until the amine and phosgene have been physically combined, preferably by mixing. In one embodiment of the invention, the solvent is added at a time or point at which at least 50%, preferably at least 80%, more preferably at least 90%, and most preferably at least 95% of the amino groups used have already undergone reaction.

The rate of the reaction between phosgene and amine or between hydrogen chloride and amine is primarily governed by the type of isocyanate to be synthesized and the reaction temperature used. Correspondingly, the addition of isocyanate acting as solvent can take place some time between 0.1 milliseconds and 10 minutes following physical combination of phosgene and amine.

In the process of the invention, some or all of the isocyanate used as solvent is added to the reaction mixture, ie the reactants amine and phosgene, only after the amine and phosgene have been physically combined. In a preferred embodiment, the portion added to the reaction mixture after the amine and phosgene have been physically combined is at least 25 wt %, preferably at least 50 wt %, more preferably at least 75 wt %, and most preferably at least 90 wt %, based on the total amount of isocyanate to be used as solvent. The portion thereof which is not to be added after the amine and phosgene have been physically combined, can be added prior to the reaction either to the amine or, preferably, to the phosgene.

In the process of the invention, use can be made of any one primary amine or a mixture of two or more such amines. Preference is given to aromatic amines, particularly those in the diaminodiphenylmethane series or their higher homologs. Examples thereof are methylenediphenylamine (MDA; individual isomers, mixture of isomers and/or oligomers thereof), toluylenediamine (TDA), n-pentylamine, 6-methyl-2-aminoheptane, cyclopentylamine, R,S 1-phenylethylamine, 1-methyl-3-phenylpropylamine, 2,6-xylidine, 2-(N,N-di-methylamino)ethylamine, 2-(N,N-diisopropylamino)ethylamine, C11-neodiamine, isophoronediamine, 3,3'-diaminodiphenylsulfone, and 4-aminomethyl-1,8-octanediamine. MDA and TDA are preferably used.

The process of the invention is thus suitable for use in the synthesis of any desired isocyanates. The process can be used with particular advantage for the production of methylene (diphenyldiisocyanate) (MDI) and toluylene-diisocyanate (TDI).

The isocyanate used as solvent is preferably the isocyanate to be synthesized. It may come from an external source or, preferably, be taken from the process of the invention and recycled. Alternatively however, other suitable isocyanates, or mixtures thereof, may be used as solvent.

An additional inert solvent can be co-used in the process of the invention. This additional inert solvent is usually an organic solvent or a mixture thereof. Chlorobenzene, dichlorobenzene, trichlorobenzene, toluene, hexane, diethyl isophthalate (DEIP), tetrahydrofuran (THF), dimethylformamide (DMF), benzene, and mixtures thereof are preferred. Particular preference is given to chlorobenzene. The additional inert solvent can be added to the amine preferably at the commencement of the reaction. The inert solvent is usually employed in a concentration of from 5 to 1000 wt %, and preferably from 50 to 500 wt %, based on the amount of amine used.

The process of the invention will now be described in detail with reference to a general flow sheet illustrating a continuous process, as shown in FIG. 1. The elements depicted in FIG. 1 are as follows:

I phosgene receiver
II amine receiver
III first mixing device
IV second mixing device
V reaction device
VI first separating device
VII second separating device
VIII isocyanate feedstock
IX phosgene purifier
X solvent purifier
1 phosgene feedline
2 amine feedline
3 inert solvent feedline
4 separated hydrogen chloride and inert solvent
5 recycled isocyanate stream
6 discharged hydrogen chloride
7 separated isocyanate
8, 11 separated inert solvent
9 purified inert solvent
10 purified phosgene The amine from amine receiver II and phosgene from phosgene receiver I are mixed in a suitable first mixing device III. The mixture of amine and phosgene is mixed, in a second mixing device IV, with isocyanate acting as solvent and passed to the reaction device V. Suitable mixing devices are, for example, nozzles or blender reactors. It is also possible to carry out the two mixing operations of mixing devices III and IV in a common mixing device but in discrete regions, as explained below with reference to the preferred embodiment illustrated in FIG. 2.

After mixing, the mixture is passed to a reaction device V. Suitable reaction devices are, for example, tubular reactors, tower reactors, reaction vessels or reaction columns. Tubular reactors are preferred. Also useful are contrivances which are both mixer and reactor, for example, tubular reactors having flanged-on nozzles.

The two separating devices VI and VII are preferably distillation units. In the first separating device VI, hydrogen chloride and, optionally, inert solvent and/or small portions of the isocyanate stream are usually separated from the isocyanate stream. In the second separating device VII, preferably inert solvent is separated and then purified (X) and recycled to amine receiver II.

Figure 2:
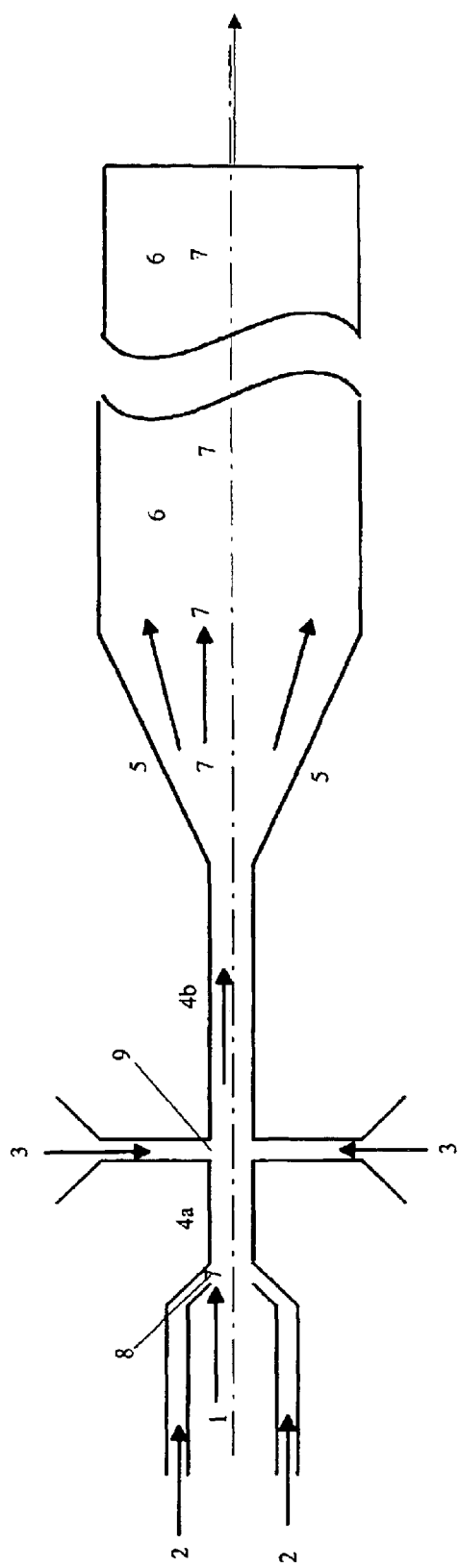

A preferred embodiment of the process of the invention involves, as illustrated in FIG. 2, the use of a mixing device described below, which is directly followed by a reaction device.

FIG. 2 illustrates a preferred assembly for the process of the invention. The elements depicted in FIG. 2 are as follows:

1 amine feed
2 phosgene feed
3 isocyanate feed
4a injector tube
4b injector tube
5 diffuser
6 tubular reactor
7 axis
8 annular gap in the phosgene feedline
9 annular gap in the isocyanate feedline In continuous phosgenation, the amine or the amine solution 1 is injected along the axis 7 into the mixing device, usually at rates of from 5 to 60 m/s. The phosgene or phosgene solution passes into the mixing device through an annular gap in the phosgene feedline 8 at rates also ranging from 5 to 60 m/s. The two streams of amine and phosgene are physically combined (corresponding to the first mixing device in FIG. 1) and passed through an optional injector tube 4a, after which isocyanate is fed in through annular gap 9 in the isocyanate feedline (corresponding to the second mixing device in FIG. 1). After passing through an optional injector tube 4b, the reaction mixture passes through diffuser 5 into tubular reactor 6. Following a residence time of from 10 s to 20 min, the resulting crude isocyanate solution is removed from the tubular reactor.

In a preferred embodiment, the injector mixing device used is an axially symmetrical injector tube device having an axial amine feed and phosgene and isocyanate feeds effected via two off-axis annular gaps.

The optimal temperature range for the process of the invention is governed, inter alia, by the type and concentration of the solvent and by the isocyanate to be synthesized. Generally, the temperature in the mixing unit is between −20° C. and 300° C., preferably between 10° C. and 200° C., and more preferably between 80° C. and 150° C. The temperature in the reactor is generally between 10° C. and 360° C., preferably between 40° C. and 210° C., and more preferably between 100° C. and 180° C. Furthermore, the absolute pressure is generally between 0.2 bar and 50 bar, preferably between 1 bar and 25 bar, and more preferably between 3 and 17 bar.

The residence time of the fluid in the mixing device and the reactor is, in all, between 12 s and 20 min, preferably in the range of from 36 s to 16 min, and more preferably between 60 s and 12 min.

The molar ratio of phosgene used to amino groups is from 1:1 to 12:1, preferably from 1.1:1 to 4:1. Amine and phosgene can be used free from solvent or dissolved in one or more of the aforementioned inert solvents. Alternatively, the phosgene can be injected as a gas into the amine solution. In addition, the phosgene may be premixed with a portion of the isocyanate used as solvent, as described above.

The amount of isocyanate used as solvent in the process of the invention is generally from 10 to 1000 wt %, preferably from 50 to 500 wt %, and more preferably from 100 to 400 wt %, based on the amount of phosgene used.

Following the reaction, the mixture of substances is separated into isocyanate, solvent, phosgene, and hydrogen chloride, preferably by means of rectification. Small amounts of by-products remaining in the isocyanate can be separated from the desired isocyanate by means of additional rectification or, alternatively, by crystallization.

Depending on the reaction conditions chosen, the crude end product may contain inert solvent, carbamoyl chloride, and/or phosgene and can be further processed by known methods (cf, eg, WO 99/40059). Furthermore, it may be advantageous to pass the product over a heat exchanger after discharge.

The invention is illustrated below by the following examples.

EXAMPLE 1

90 g of a toluylenediamine mixture (TDA mixture), comprising 80 wt % 2,4-TDA and 20 wt % 2,6-TDA was dissolved in 360 g of monochlorobenzene (MCB). The resulting TDA solution was injected into the mixing device illustrated in FIG. 2 along the axis at a rate of 30 m/s and a throughput of 1.8 L/h, at a temperature of 50° C. Simultaneously, 1.6 kg of a 25% strength phosgene solution, which had been produced from 400 g of phosgene and 1.2 kg of MCB, were injected at a temperature of 30° C. through the first annular gap of the nozzle mixer at a rate of 30 m/s and at an angle of 45° to the axis. Then 1.2 kg of toluylene-diisocyanate, comprising 80 wt % 2,4-TDI and 20 wt % 2,6-TDI, were injected at a temperature of 30° C. into the axial injector tube through the second annular gap at an angle of 90° to the axis of the mixing device and at a rate of 25 m/s in the plane of entry. The mixture passed directly from the nozzle mixer into a tubular reactor, which had a capacity of ca 300 mL and a length of 24 m and provided a residence time for the total mixture of ca 1.4 min and was kept at a temperature of from ca 130° to 140° C. Before and after synthesis, the apparatus was continuously rinsed with monochlorobenzene as inert solvent. Following removal, by distillation, of the phosgene and chlorobenzene, TDI was isolated at a purity of ca 99.2% (GC) and a yield of 99.1%. The phosgene hold-up in the reactor was, based on the incoming phosgene mass flow, not more than ca 38 g. This value was calculated on the assumption that phosgene was not consumed during the reaction. This gave a phosgene hold-up of ca 76 g for a production output of 1 kg of TDI per hour.

COMPARATIVE EXAMPLE 2 USING AN ISOCYANATE/PHOSGENE SOLUTION

In a manner similar to that described in Example 1, 90 g of a toluylenediamine mixture (TDA mixture) comprising 80 wt % 2,4-TDA and 20 wt % 2,6-TDA were dissolved in 360 g of monochlorobenzene. The resulting TDA solution was injected into the mixing device illustrated in FIG. 2 along the axis at a rate of 30 m/s and a throughput of 1.8 L/h, at a temperature of 50° C. Simultaneously, 1.6 kg of a 25% strength phosgene solution, which had been produced from 400 g of phosgene and 1.2 kg of toluylene diisocyanate, comprising 80 wt % 2,4-TDI and 20 wt % 2,6-TDI, were injected at a temperature of 30° C. through the first annular gap of the nozzle mixer at a rate of 30 m/s and at an angle of 45° to the axis. The mixture passed directly from the nozzle mixer into a tubular reactor, which had a capacity of ca 180 mL and a length of 14.4 m and provided a residence time for the total mixture of ca 1.4 min and was kept at a temperature of from ca 130° to 140° C. Before and after synthesis, the apparatus was continuously rinsed with monochlorobenzene as inert solvent. Following removal, by distillation, of the phosgene and chlorobenzene, TDI was isolated at a purity of ca 99.1% (GC) and a yield of 98.5%. The phosgene hold-up in the reactor was, based on the incoming phosgene mass flow, not more than ca 38 g. This value was calculated on the assumption that phosgene was not consumed during the reaction. This gave a phosgene hold-up of ca 76 g for a production output of 1 kg of TDI per hour.

COMPARATIVE EXAMPLE 3 USING A MCB-PHOSGENE SOLUTION

In a manner similar to that described in Example 1, 90 g of a toluylenediamine mixture (TDA mixture) comprising 80 wt % 2,4-TDA and 20 wt % 2,6-TDA were dissolved in 360 g of monochlorobenzene. The resulting TDA solution was injected into the mixing device illustrated in FIG. 2 along the axis at a rate of 30 m/s and a throughput of 1.8 L/h, at a temperature of 50° C. Simultaneously, 1.6 kg of a 25% strength phosgene solution, which had been produced from 400 g of phosgene and 1.2 kg of MCB, were injected at a temperature of 30° C. through the first annular gap of the nozzle mixer at a rate of 30 m/s and at an angle of 45° to the axis. The mixture passed directly from the nozzle mixer into a tubular reactor, which had a capacity of ca 375 mL and a length of 30 m and provided a residence time for the total mixture of ca 2.7 min and was kept at a temperature of from ca 130° to 140° C. Before and after synthesis, the apparatus was continuously rinsed with monochlorobenzene as inert solvent. Following removal, by distillation, of the phosgene and chlorobenzene, TDI was isolated at a purity of ca 99.1% (GC) and a yield of 97.4%. The phosgene hold-up in the reactor was, based on the incoming phosgene mass flow, not more than ca 72 g. This value was calculated on the assumption that phosgene was not consumed during the reaction. This gave a phosgene hold-up of ca 147 g for a production output of 1 kg of TDI per hour.

SUMMARY OF THE EXAMPLES

Table 1 below compares the results of Example 1 and Comparative Examples 2 and 3. Table 1 clearly shows that the process of the invention leads to a rise in selectivity without raising the phosgene hold-up or lowering the space-time yield.

| Example | Example 1 | Comparative Example 2 | Comparative Example 3 |
| --- | --- | --- | --- |
| Phosgene hold-up for a production output of 1 kg/h | 76 g | 76 g | 147 g |
| Yield | 99.2% | 98.5% | 97.4 |
| Distillation purity | 99.1% | 99.1% | 99.1% |

What is claimed is:

1. A process for the production of isocyanates by reaction of primary amines with phosgene, in which isocyanate is used as solvent, wherein some or all of the isocyanate used as solvent is added to the reactants only after the amine and phosgene have been physically combined.

2. A process as defined in claim 1, which is carried out continuously.

3. A process as defined in claim 1, wherein portions of the isocyanate produced are recycled and used as solvent.

4. A process as defined in claim 1, wherein the amount of isocyanate added to the reaction mixture only after the amine and phosgene have been physically combined is at least 25 wt %, based on the total amount of isocyanate used as solvent.

5. A process as defined in claim 1, wherein the amine used is methylenedi(phenylamine) or toluylenediamine.

6. A process as defined in claim 1, wherein the reaction of amine with phosgene is carried out in a tubular reactor having an upstream injector mixing device.

7. A process as defined in claim 6, wherein the injector mixing device used is an axially symmetrical injector tube device having an axial amine feed and phosgene and isocyanate feeds effected through two off-axis annular gaps.

* * * * *